United States Patent [19]
Wysong

[11] 4,163,105
[45] Jul. 31, 1979

[54] ARYLOXYMETHYL IMIDAZOLINES

[75] Inventor: Don V. Wysong, Farwell, Mich.

[73] Assignee: The Dow Chemical Company, Midland, Mich.

[21] Appl. No.: 623,179

[22] Filed: Oct. 16, 1975

[51] Int. Cl.$^2$ ............................................ C07D 233/22
[52] U.S. Cl. .................................. 548/342; 424/273 R
[58] Field of Search ....................... 260/309.6; 548/342

[56] References Cited

U.S. PATENT DOCUMENTS

| 3,449,354 | 6/1969 | White | 260/309.6 |
|---|---|---|---|
| 3,449,356 | 6/1969 | White | 260/309.6 |
| 3,449,357 | 6/1969 | White | 260/309.6 |

FOREIGN PATENT DOCUMENTS 1935479  1/1971  Fed. Rep. of Germany ........ 260/309.6

Primary Examiner—Alan L. Rotman
Attorney, Agent, or Firm—James W. Ambrosius

[57] ABSTRACT

The compounds 4[(4,5-dihydro-2-1H-imidazolyl)-methoxy]-N,N,2-trimethylbenzeneamine and 2[(3-trifluoromethylphenoxy)methyl]-2-imidazoline and their pharmaceutically-acceptable salts are described. The compounds are useful as alcohol antagonists in animals and in various agricultural applications.

3 Claims, No Drawings

ARYLOXYMETHYL IMIDAZOLINES

SUMMARY OF THE INVENTION

The present invention is directed to novel aryloxymethyl imidazoline compounds having the following formulae:

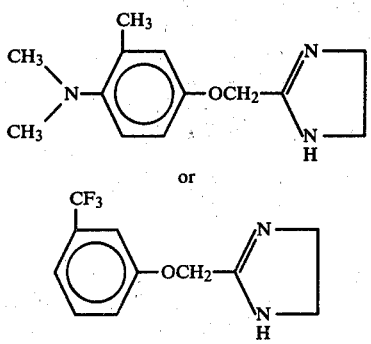

and the pharmaceutically-acceptable salts thereof.

It has been found that the compound of formula I, 4[(4,5-dihydro-2-1H-imidazolyl)methoxy]-N,N,2-trimethylbenzenamine, and formula II, 2[3-trifluoromethylphenoxy)-methyl]-2-imidazoline and the pharmaceutically-acceptable salts thereof have the useful property of antagonizing the central nervous system depressant effects of ethanol when administered to animals, and in particular to mammals intoxicated or narcotized with ethanol. An added advantage is that these compounds have relatively low toxicity in animals.

Further it has been shown that 2[(3-trifluoromethylphenoxy)methyl]-2-imidazoline is an effective nematocide, arachicide, and fungicide. The compound 4[(4,5-dihydro-2-1H-imidazolyl)methoxy]-N,N,-2-trimethyl-benzenamine also has utility as a herbicide and is particularly effective in the control and killing of yellow foxtail.

As employed herein, the terms "pharmaceutically-acceptable salts" refers to non-toxic acid addition salts of the imidazoline compounds, the anions of which are relatively innocuous to animals at dosages consistent with good ethanol antagonizing activity so that beneficial effects of the free base are not vitiated by side effects ascribable to the anions. Pharmaceutically-acceptable salts include those derived from mineral acids such as hydrochloric, hydrobromic, sulfuric, and nitric acids and from organic acids such as acetic, lactic, maleic, succinic, fumaric, glutaric, citric, malic, p-toluenesulfonic and tartaric acids, and the like.

PRIOR ART

Aryloxymethyl imidazolines having trifluoromethyl and amino substitutions or various halo substitutions on the phenyl ring have been described in U.S. Pat. Nos. 3,423,422; 3,449,354; 3,449,355; and 3,449,356.

Further certain aryloxymethyl imidazolines have been described as having pharmacodynamic activity particularly analgesic and anti-inflammatory activity. See U.S. Pat. Nos. 3,423,423 and 3,449,501. Recently, however, ethanol antagonist activity has been recognized in the imidazoline compound, 2-[3,4-dichlorophenoxy)methyl]-2-imidazoline as disclosed in U.S. Pat. No. 3,860,719. It is readily apparent that the activity as an alcohol antagonist of the presently disclosed novel compounds is not suggested or expected from the above-listed patents.

DETAILED DESCRIPTION OF THE INVENTION

The compounds of the present invention are white to buff-colored crystalline solids the salts of which are soluble in water. In general they are prepared in two steps by reacting a selected phenol with chloroacetonitrile to give a substituted tolyloxyacetonitrile. This product is then reacted with ethylenediamine monotosylate to give the corresponding aryloxymethyl imidazoline. The reactions are illustrated below.

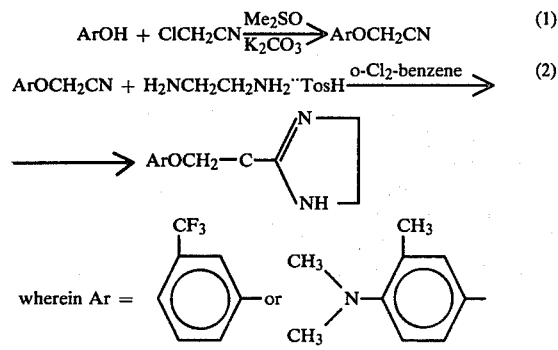

The tosylate can be converted to the free base by making the reaction mixture basic. The free base can be further purified by conventional methods such as recrystallization, or it can be converted to a pharmaceutically-acceptable salt.

The pharmaceutically-acceptable salts of the disclosed compounds can be prepared by conventional procedures such as dissolving the free base in a minimal amount of alcohol and adding an alcohol solution of an acid such as hydrochloric acid, hydrobromic acid, malic acid, maleic acid, or succinic acid until precipitation of the corresponding salt is complete. The salt can be further purified by recrystallization or converted to the free base by hydrolysis.

The imidazoline is used by administering the compound internally to an animal in a manner effective to introduce an effective ethanol-antagonizing amount into the blood stream, usually by injection or by oral administration. Ethanol antagonism can be achieved when the compound is administered prior to administration or consumption of ethanol, provided the ethanol is introduced into the animals' system at a time when the remaining blood level of the imidazoline is sufficient to achieve alcohol antagonizing effect.

The amount of the imidazoline compound to be administered to a mammal in a particular case can vary depending upon such factors as the ethanol blood level, degree of intoxication or narcosis to be alleviated, the presence of ethanol in the gastrointestinal tract, the route of administration, the exact effect to be produced, whether or not the free base or a pharmaceutically-acceptable salt or the mixed imidazoline is employed, whether or not the compound is employed prophylactically or therapeutical e.g., as an antidate, and the species, size, weight, age, and physical condition of the particular animal being treated. In mice quantities of 10 mg/kg of body weight were found to be effective when injected intraperitoneally.

The imidazoline compound can be formulated with conventional pharmaceutical carriers in known procedures. The selection of the exact carrier to be employed in any given circumstance can be carried out by standard and conventionally employed range finding operations to provide formulations having the desired characteristics of physical form, ease of administration by desired route, storage stability, etc.

The compound 2[(3-trifluoromethylphenoxy)methyl]-2-imidazoline is also effective as an arachicide, fungicide, and nematocide. At a concentration of 500 ppm the compound is effective in the control and killing of two spotted spider mites and the fungus *Trichophton mentagrophytes*. At a concentration of 12 ppm the compound will kill and control rootknot nematodes (*Meloidogne incognita var. acrita*) in the soil. The compound 4[(4,5-dihydro-2-1H-imidazolyl)methoxy]-N,N,2-trimethylbenzenamine has proven to be an effective herbicide. At a concentration of 4000 ppm the compound is particularly effective in the control and killing of yellow foxtail.

The following examples illustrate a preferred route for preparing the compounds of the present invention but, as such, are not to be construed as limitations upon the overall scope of the same.

EXAMPLE 1

Preparation of
4[(4,5-dihydro-2-1H-imidazolyl)-methoxy]-N,N,2-trimethylbenzenamine hydrochloride (a) Preparation of Acetonitrile Intermediate 30.2 Grams of 4-dimethylamino-m-cresol and 16.0 grams of chloroacetonitrile were dissolved in 50 ml. of dimethylsulfoxide. Anhydrous $K_2CO_3$ (39.6 g) was added as a catalyst. The mixture was heated with stirring to 70°–80° C. for three hours. The reaction mixture was poured into approximately 2 liters of a ice and water mixture. The product was extracted with methylene chloride. The extract was dried with SEA SORB ® and activated charcoal and the resulting mixture was filtered. The filtrate was dried under vacuum to yield 4-dimethylamino-m-tolyloxyacetonitrile.

(b) Preparation of the Imidazoline Salt

The intermediate prepared above (23.8 grams) was dissolved in 110 ml. of dichlorobenzene and mixed with 29.2 grams of ethyleneamine monotosylate. This charge was heated with stirring and refluxed for 1.5 hours under nitrogen. Ammonia was collected as it was liberated. The reaction mixture was evaporated to dryness under vacuum, and the residue was dissolved in water and the resulting solution made basic. The aqueous system was extracted with methylene chloride. This extract was dried with SEA SORB ® and activated charcoal and was filtered. The filtrate was evaporated to dryness under vacuum leaving a viscous oil that crystallized on cooling. The 4[(4,5-dihydro-2-1H-imidazolyl)methoxy]-N,N,-trimethylbenzenamine product was recrystallized from cyclohexane. The purified product was dissolved in isopropyl alochol to which hydrochloric acid in isopropyl alochol was added until a pH of 6.5 was obtained. The salt precipitated out of solution and was filtered off.

The melting point of the free base was 67°–68° C. while that for the hydrochloride was 200°–202° C. NMR data was consistent with the structure of the disclosed compound. Molecular titration was also used to confirm the disclosed compound.

EXAMPLE 2

Preparation of
2-[(3-trifluoromethylphenoxy)-methyl]-2-imidazoline hydrochloride (a) Preparation of Acetonitrile Intermediate A quantity (32.4 grams) of m-hydroxybenzotrifluoride and 16.0 grams of chloroacetonitrile were dissolved in 50 ml. of dimethylsulfoxide. Anhydrous $K_2CO_3$ (39.6 grams) was added to the solution to act as a catalyst. The reaction mixture was held at 70° to 80° C. for 3 hours. The heat of reaction was sufficient at first to require cooling the reaction mixture. The reaction mixture was poured into 1000 grams of an ice and water mixture. The product was extracted with methylene chloride. The extract was dried with SEA SORB® and activated charcoal and was filtered. The filtrate was evaporated under vacuum to leave the α,α,α-trifluoro-m-toloxyacetonitrile.

(b) Preparation of the Imidazoline Salt 20.1 Grams of the intermediate prepared above was dissolved in 75 ml of dichlorobenzene and mixed with 23.3 grams of ethylenediamine monotosylate. This charge was heated with stirring and refluxed for 1 hour under nitrogen. Ammonia was collected as it was liberated. The reaction mixture was cooled with stirring and diluted with methylene chloride and cooled further to 5° C. The crystals of 2[3-trifluoromethylphenoxy)methyl]-2-imidazoline that formed were filtered off and washed with methylene chloride and dried under vacuum. The crystals were dissolved in water and basified with NaOH. The basified product was extracted with methylene chloride and the extract dried with SEA SORB ® and activated charcoal. The extract was filtered. The filtrate was concentrated to dryness leaving a viscous oil that crystallized on cooling. The crystals were dissolved in isopropyl alcohol and acidified with HCl in isopropanol. The 2[3-trifluoromethylphenoxy)methyl]-2-imidazoline hydrochloride precipitated and was filtered off.

The melting point of the hydrochloride salt was 231° to 233° C. NMR data was consistent with the structure of the disclosed compound. Molecular titration was also used to confirm the disclosed compound.

In a similar manner the free base of 4[(4,5-dihydro-2-1H-imidazolyl)methoxy]-N,N,2-trimethylbenzenamine and 2[(3-trifluoromethylphenoxy)methyl]-2-imidazoline compounds can be treated with hydrobromic, sulfuric, nitric, acetio, lactic, maleic, succinic, fumaric, glutaric, citric, malic, p-toluenesulfonic or tartaric acid to provide the corresponding pharmaceutically-acceptable salt.

I claim:

1. An aryloxymethyl imidazoline having the formula

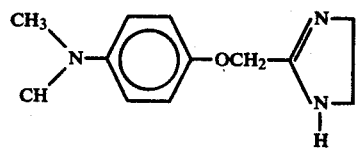

and the pharmaceutically-acceptable salts thereof.

2. The compound of claim 1 wherein the compound is 4[(4,5-dihydro-2-1H-imidazolyl)methoxy]-N,N,-2-trimethylbenzenamine.

3. The compound of claim 1 wherein the compound is 4[(4,5-dihydro-2-1H-imidazolyl)methoxy]-N,N,2-trimethylbenzenamine hydrochloride.

* * * * *

UNITED STATES PATENT AND TRADEMARK OFFICE
CERTIFICATE OF CORRECTION

PATENT NO. : 4,163,105

DATED : July 31, 1979

INVENTOR(S) : Don V. Wysong

It is certified that error appears in the above-identified patent and that said Letters Patent are hereby corrected as shown below:

In the Abstract, line 2, "2-trimethylbenzeneamine" should read -- 2-trimethylbenzenamine -- .

Column 1, line 28, "phenoxy)-methyl]-2-imidazoline" should read -- phenoxy)methyl]-2-imidazoline -- .

Column 1, line 38, "dihydro-2-1H-imidazolyl)methoxy]-N,N,-2-trimethyl-" should read -- dihydro-2-1H-imidazolyl)methoxy]-N,N,2-trimethyl- -- .

Column 2, line 64, "antidate" should read -- antidote -- .

Column 3, line 29, "4[(4,5-dihydro-2-1H-imidazolyl)-methoxy]-N,N,2-" should read -- 4[(4,5-dihydro-2-1H-imidazolyl)methoxy]-N,N,2- -- .

Column 3, line 58, "imidazolyl)methoxy]-N,N-trimethylbenzenamine" should read -- imidazolyl)methoxy]-N,N,2-trimethylbenzenamine -- .

UNITED STATES PATENT AND TRADEMARK OFFICE
CERTIFICATE OF CORRECTION

PATENT NO. : 4,163,105
DATED : July 31, 1979
INVENTOR(S) : Don V. Wysong

It is certified that error appears in the above-identified patent and that said Letters Patent are hereby corrected as shown below:

Column 4, line 4, "2-[(3-trifluoromethylphenoxy)-methyl]-2-imidazoline" should read -- 2-[(3-trifluoromethylphenoxy)methyl]-2-imidazoline -- .

Column 4, line 47, "acetio" should read -- acetic -- .

Column 4, line 55, " 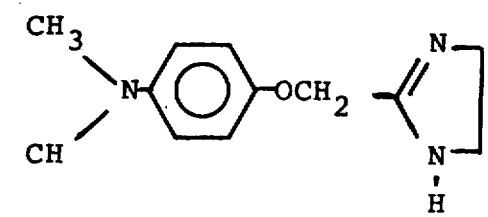 "

should read 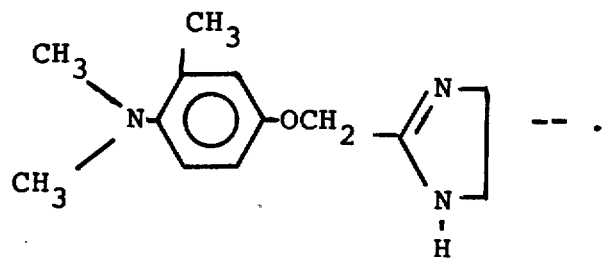 -- .

UNITED STATES PATENT AND TRADEMARK OFFICE
CERTIFICATE OF CORRECTION

PATENT NO. : 4,163,105
DATED : July 31, 1979
INVENTOR(S) : Don V. Wysong

It is certified that error appears in the above-identified patent and that said Letters Patent are hereby corrected as shown below:

Column 4, line 63, "4[(4,5-dihydro-2-1H-imidazolyl)methoxy]-N,N,-2- " should read -- 4[(4,5-dihydro-2-1H-imidazolyl)methoxy]-N,N,2- -- .

Signed and Sealed this

Eighteenth Day of March 1980

[SEAL]

Attest:

SIDNEY A. DIAMOND

Attesting Officer  Commissioner of Patents and Trademarks